United States Patent
Caskey et al.

(10) Patent No.: US 10,450,244 B2
(45) Date of Patent: Oct. 22, 2019

(54) METHOD FOR OXYGEN REMOVAL FROM HYDROGEN USING ADSORBENT

(71) Applicant: UOP LLC, Des Plaines, IL (US)

(72) Inventors: Stephen Caskey, Lake Villa, IL (US); Vladislav I. Kanazirev, Arlington Heights, IL (US); Thomas Traynor, Vernon Hills, IL (US)

(73) Assignee: UOP LLC, Des Plaines, IL (US)

( * ) Notice: Subject to any disclaimer, the term of this patent is extended or adjusted under 35 U.S.C. 154(b) by 414 days.

(21) Appl. No.: 15/342,775

(22) Filed: Nov. 3, 2016

(65) Prior Publication Data

US 2017/0174514 A1 Jun. 22, 2017

Related U.S. Application Data

(60) Provisional application No. 62/268,174, filed on Dec. 16, 2015.

(51) Int. Cl.

| | |
|---|---|
| *C01B 3/56* | (2006.01) |
| *C07C 7/12* | (2006.01) |
| *B01D 53/04* | (2006.01) |
| *B01D 53/46* | (2006.01) |
| *C01G 45/02* | (2006.01) |
| *C01G 49/02* | (2006.01) |
| *C01G 53/04* | (2006.01) |
| *C01G 51/04* | (2006.01) |
| *B01J 20/06* | (2006.01) |
| *B01J 20/30* | (2006.01) |
| *B01J 20/12* | (2006.01) |
| *B01D 53/02* | (2006.01) |
| *C01B 3/50* | (2006.01) |
| *C01B 13/02* | (2006.01) |

(52) U.S. Cl.
CPC ............... *C07C 7/12* (2013.01); *B01D 53/02* (2013.01); *B01D 53/04* (2013.01); *B01D 53/46* (2013.01); *B01J 20/06* (2013.01); *B01J 20/12* (2013.01); *B01J 20/3042* (2013.01); *B01J 20/3085* (2013.01); *C01B 3/50* (2013.01); *C01B 13/0281* (2013.01); *C01G 45/02* (2013.01); *C01G 49/02* (2013.01); *C01G 51/04* (2013.01); *C01G 53/04* (2013.01); *B01D 2253/112* (2013.01); *B01D 2256/16* (2013.01); *B01D 2256/20* (2013.01); *B01D 2256/245* (2013.01); *B01D 2257/104* (2013.01); *C01B 2203/042* (2013.01); *C01B 2203/0465* (2013.01)

(58) Field of Classification Search
CPC .... B01D 53/04; B01D 53/46; B01D 2257/00; B01D 2257/104; B01D 2257/502; B01D 2257/108; B01D 2257/702; B01D 2253/00; B01D 2256/16; B01D 2256/245; B01D 2256/20; B01J 20/06; B01J 20/12; B01J 20/30; B01J 20/3085; B01J 20/3042; B01J 20/043; C01B 2203/042; C01B 2203/0465; C01B 3/56; C01B 3/50; C01G 45/02; C01G 49/02; C01G 53/04
See application file for complete search history.

(56) References Cited

U.S. PATENT DOCUMENTS

| | | | |
|---|---|---|---|
| 3,361,531 A * | 1/1968 | Erb | A23L 3/3436 423/219 |
| 5,891,220 A | 4/1999 | Gary | |
| 7,160,360 B2 | 1/2007 | Wu et al. | |

FOREIGN PATENT DOCUMENTS

| | | |
|---|---|---|
| CN | 100360209 C | 1/2008 |
| JP | 2144114 A | 6/1990 |
| JP | 6087766 A | 3/1994 |

OTHER PUBLICATIONS

JP6087766 A2, 1994, Keiichi et al, machine translation (Year: 1994).*

Augustin, Matthias et al., "Mechanistic study on the activity of manganese oxide catalysts for oxygen reduction reaction in an aprotic electrolyte", Electrochimica Acta, v 158, p. 383-389, Mar. 10, 2015; ISSN: 00134686; DOI: 10.1016/j.electacta.2015.01.163; Publisher: Elsevier Ltd.

Lu, Min et al., "Carbon nanotube supported MnO2 catalysts for oxygen reduction reaction and their applications in microbial fuel cells", Biosensors and Bioelectronics, v 26, n 12, p. 4728-4732, Aug. 15, 2011; ISSN: 09565663, E-ISSN: 18734235; DOI: 10.1016/j.bios.2011.05.036; Publisher: Elsevier Ltd.

* cited by examiner

*Primary Examiner* — Melvin C. Mayes
*Assistant Examiner* — Smita S Patel

(57) ABSTRACT

The present subject matter relates generally to a method for the removal of oxygen from hydrogen using a manganese, iron, nickel or cobalt based adsorbent. More specifically, the present subject matter relates to the methods for the removal of oxygen from hydrogen using a manganese based adsorbent without the generation of water or other oxides.

7 Claims, No Drawings

METHOD FOR OXYGEN REMOVAL FROM HYDROGEN USING ADSORBENT

CROSS-REFERENCE TO RELATED APPLICATION

This application claims priority from Provisional Application No. 62/268,174 filed Dec. 16, 2015, the contents of which are hereby incorporated by reference.

BACKGROUND

The present subject matter relates generally to a method for the removal of oxygen from hydrogen using a manganese, iron, nickel or cobalt based adsorbent. More specifically, the present subject matter relates to the methods for the removal of oxygen from hydrogen using a manganese based adsorbent without the generation of water or other oxides.

Hydrocarbons and hydrogen used in industry should be as pure as possible without the presence of contaminants. Conventionally, oxygen is a contaminant in hydrogen and some hydrocarbon feedstocks. The purification of hydrogen is needed for many refining and petrochemical applications. There have been several absorption systems proposed and used for removal of oxygen from gas mixtures, but each is characterized by important limitations. For example, certain systems require elevated temperatures for effective removal and this requires additional heating equipment if the feed gas is available at ambient temperature. Another disadvantage of conventionally known oxygen removal systems is their inability to provide an oxygen free product without addition of other impurities during this removal. Certain end uses of the hydrogen gas require complete removal of trace amounts of oxygen without simultaneous introduction of other impurities.

The previously employed oxygen adsorbents for removal of oxygen from hydrogen and hydrocarbons have a tendency to pulverize easily and cause powder carryover from the adsorbent chamber into the product gas system. Besides the contamination problem, attrition of the adsorbent reduces the overall efficiency. Therefore, there is a need to remove oxygen contaminants from hydrogen gas completely to meet the product gas specifications for commercial use.

Typically, the copper based adsorbents used to remove oxygen from the feeds will often lead to water generation as the copper oxides react with hydrogen to form elemental copper and water. Copper oxides are particularly susceptible to reduction especially by hydrogen at lower temperatures depending on the partial pressure. This reaction of copper oxides with hydrogen will generate unwanted water which needs to be removed to meet product specifications. Therefore, there is a need for an improved method for removing oxygen from oxygen containing hydrogen gas streams without generation of water.

SUMMARY

An embodiment of the subject matter is a process for removing oxygen from an oxygen containing gas mixture comprising the steps of providing a partially oxidized form of manganese carbonate, iron carbonate, nickel carbonate and/or cobalt carbonate. The partially oxidized form of manganese carbonate, iron carbonate, nickel carbonate and/or cobalt carbonate is contacted with the gas mixture. The oxygen from the gas mixture is adsorbed without generation of water or other oxygenates such as $CO_2$ or $CO$ to produce a purified gas.

Another embodiment of the subject matter is a process for preparing an improved adsorbent for removing oxygen comprising providing a precursor selected from the group consisting of manganese carbonate, iron carbonate, cobalt carbonate, and nickel carbonate. About 15-20% water is added and mixed to the precursor to generate a mull LOI of 45-55% to prepare a mixture. The mixture is mulled and formed. The mixture is dried to about 0.5-3% water. The precursor is partially decomposed to suboxides.

A process is provided for removal of oxygen from an oxygen containing gas mixture using an adsorbent selected from the group consisting of manganese carbonate, iron carbonate, nickel carbonate, cobalt carbonate and a mineral clay binder. The bed is contacted with hydrogen containing gas at temperatures below 400° C., preferably about 150° C. to about 350° C., thereby reducing the carbonate to an oxide compound. The bed is purged with an inert gas to remove residual hydrogen. The feed gas mixture is contacted with the oxide compound containing bed at substantially ambient temperatures thereby adsorbing the oxygen and oxidizing the oxide compound to a higher cationic valence state. The purified product gas and the oxidized bed are then separated and the product gas used as desired.

The present invention seeks to provide an improved process for removing oxygen from oxygen containing gas mixture by contact with a solid adsorbent at ambient or near ambient temperature. A benefit of the present subject matter is a process that enables removal of oxygen from oxygen containing gas mixture without generation of water or other oxygenates. These and other features, aspects, and advantages of the present subject matter will become better understood upon consideration of the following detailed description, and appended claims.

DETAILED DESCRIPTION

The gas mixtures used in refining and petrochemical applications are generally contaminated with oxygen. The use of copper based adsorbents to remove oxygen from the gas mixtures contaminated with oxygen leads to water generation that is undesired. Therefore, oxygen and water are undesirable contaminant that needs to be removed from gas mixtures comprising hydrogen to meet the product specification of gas mixtures for commercial use.

The present subject matter provides an improved method to remove oxygen from oxygen containing gas mixtures without generation of water. The gas mixture may comprise from about 1 to about 100 ppm oxygen. The gas mixture may comprise hydrocarbons such as methane and carbon monoxide. The present subject matter uses manganese oxide (MnO), iron carbonate, nickel carbonate and/or cobalt carbonate that can react with oxygen at a moderate temperature for adsorption of oxygen from the gas mixtures. The benefit of the present subject matter is that the oxidized form of the adsorbent such as manganese oxide (i.e. $Mn_3O_4$) is not susceptible to reduction until higher temperatures and therefore will not generate water. This eliminates the need to remove water which would eliminate the need for a dehydration vessel.

Manganese oxide (MnO) may be obtained from reduction of manganese dioxide ($MnO_2$) with hydrogen. However, this source of manganese oxide is characterized by prohibitively low oxygen loadings and must be regenerated frequently unless extremely large beds are used. Moreover, it generally exists in the powder form which is too finely divided for commercial systems involving gas flow through large fixed beds. In an attempt to avoid this problem, manganese dioxide powder may be dispersed on shredded fiber and packed in a tube. During the reduction to MnO the mixture was sintered. However, when the bed was cooled a slight shrinkage occurred with the result that the bed separated from the walls of the tube exposing only the outer surface of the sintered fiber MnO mass to gases flowing through the tube. As a consequence, the oxygen loading was prohibitively low.

A formed sample of manganese carbonate may be decomposed in a hydrogen containing stream at temperatures of about 20° C. to about 400° C. The crystallite size of the MnO generated must be of small size of at most 800 Angstrom (0.08 microns). This material is then used in the removal of oxygen at temperatures between ambient to 200° C. by which oxygen is removed without generation of water. This process of steam free oxygen can be used directly without further use of dehydration vessel.

It has been unexpectedly found that remarkably high oxygen absorption capacities are afforded by oxides of manganese when prepared by reduction of its carbonate compound. This phenomena is believed to be due to release of the relatively large carbon dioxide molecule which may structurally change and opening up the compound's lattice arrangement leaving voids larger than oxygen atoms, thus increasing its surface area. It has also been found that the open lattice structure of manganous oxide may be formed in the presence of mineral clay compound and a shaped compact body of high attrition resistance may be prepared which possesses high absorptive capacity.

Another embodiment of the invention provides a method for preparing an improved adsorbent comprising the steps of initially providing a mixture of manganese carbonate, and about 5% to about 25% mineral binder, and thoroughly mulling the constituents. About 20 wt % to 30 wt % water is then added and mixed to prepare a second mixture. A shaped compact body may be formed from the second mixture. The second mixture is then dried to about 1% to 3 wt % water. The dried second mixture is thereafter contacted with a hydrogen containing gas at ambient to about 400° C. for sufficient duration to convert the manganese carbonate to an oxide compound. The resulting adsorbent body possesses an open lattice structure and high attrition resistance. Moreover, the physical stability of the oxide is not affected by repeated activations.

Examples of mineral clays which may be employed for bonding a manganese compound without substantially altering the adsorptive properties of the oxide are attapulgite, kaolin, sepiolite, polyharskite, koilinite, plastic ball clays, clays of attapulgite or kaolin types, bentonite, montmorillonite, illite, chlorite, and bentonite-type clay. The mineral clay used in the present subject matter is a bonded shaped contact body and maintains its strength when heated repeatedly to high temperatures for periodic regeneration by reduction of the oxide to a lower cationic valence state. Also, the clay should be semi-plastic or plastic in the presence of air at atmospheric temperatures to permit compacting and shaping, and capable of acquiring a substantial "green" strength upon exposure for short periods of time to elevated temperature drying conditions.

Among the mineral clay binders, attapulgite afforded the strongest oxygen adsorbent bodies, and is the preferred binder material for the manganese compound. The mineral clay binder should comprise between about 5 and about 25 wt % of the first mixture. Less than about 5 wt % clay does not provide sufficient plasticity for shaping or a sufficiently strong adsorbent body, and more than about 25 wt % clay does not appreciably improve the body strength and unnecessarily dilutes the body. That is, the mineral clay binder does not itself act as an oxygen adsorbent. An attapulgite content of about 10 wt % is preferred with manganese carbonate, as affording both satisfactory body strength and high bulk adsorption capacity.

The manganese carbonate and the clay binder (if employed) are mixed for sufficient duration to obtain uniform distribution of the components. As used herein, "mixing" refers to powdering, pulverizing, crushing, or grinding of the components so that the individual particles of the mulled first mixture are small enough to pass through a 50 U.S. standard mesh screen. This is necessary for intimate contact between the carbonate and mineral clay components, and to permit the subsequent forming of a compact body. It has been found that mixing periods of about 30 minutes are sufficient to reach the desired state of intimate contact.

After mixing of the first mixture, sufficient water is added to provide a second mixture having between about 15 and about 30 wt % water. The latter is uniformly dispersed in the carbonate-clay binder mixture to prepare a shapeable mass. If less than 15 wt % water is added, the mass does not possess sufficient fluidity for easy shaping, as for example by extrusion. On the other hand, more than about 30 wt % water results in an excessively fluid mix and will not retain its shape. About 25 wt % water is preferred as an optimum balance.

In forming the second mixture into a compact body, several techniques may be used, as for example molding, extruding, tumbling, drum-rolling, casting, slip-casting, disk-forming, prilling, tableting and briquetting. The following are possible shapes of the oxygen absorbent mass: beads, spheres, pellets, tablets, sheets, flakes, briquettes, granules, cylinders, tubes, disks, partitions, toroids, cubes and blocks. Before conducting the shaping step, it may be desirable to intermix small amounts of other materials such as lubricants, extrusion aids, gelling or thickening agents, surface active agents and the like.

After the shaping step, the shaped contact bodies are dried at suitable elevated temperature of about 100° C. to reduce the water content to about 0.5 to about 3 wt %. Drying may be performed in an externally fired oven. The dried, shaped bodies may then be broken into smaller particles if desired, or alternatively placed in a reactor for contact with a hydrogen containing gas a temperature of about ambient to about 400° C. If higher temperatures are employed, the reduced manganese oxide-clay binder mass may sinter or coalesce. This needs to be avoided as sintering tends to close the voids created by release of carbon dioxide gas and are necessary for high oxygen absorption capacity. In order to provide a closely controllable reduction, it is usually preferable to dilute the hydrogen with an inert gas, as for example nitrogen. A reducing gas atmosphere of 15% hydrogen and 85% nitrogen may be found satisfactory.

The properties of the different manganese phase, binder are illustrated in Table 1 below.

TABLE 1

| Property | Sample 1 | Sample 2 | Sample 3 |
| --- | --- | --- | --- |
| Mn | $MnCO_3$ | $Mn_2O_3/Mn_3O_4$ | $MnO/MnCO3$ |
| Binder | Attapulgite clay | Attapulgite clay | Attapulgite clay |
| Form | ⅛" cylinder | ⅛" cylinder | ⅛" cylinder |

TABLE 1-continued

| Property | Sample 1 | Sample 2 | Sample 3 |
|---|---|---|---|
| Color | Tan | Brown | Brown |
| Bulk density (g/cc) | 1.0 | 0.74 | — |
| Bulk density (lb/ft3) | 62.4 | 46.1 | — |

The $MnCO_3$ to MnO reaction is a thermal decomposition reaction. The $MnCO_3$ thermally decomposes to form MnO and $CO_2$ without reduction. However, in the absence of $H_2$, before $CO_2$ escapes from the system, it can be reduced to CO by the MnO which in turn is oxidized to $Mn_2O_3$. The major constituent of the oxygen containing gas mixture may be chemically inactive or active, only limitation being that it does not react with manganese oxide absorbent mass, in preference to oxygen. The halogen gases such as chlorine and fluorine are excluded as carbon dioxide and certain sulfur compounds, for example $H_2S$ and $SO_2$. The extent to which a particular oxide of manganese is formed by contact with oxygen depends on temperature, partial pressure of oxygen, and contact time. The oxides of manganese combine with oxygen according to the following equation, and their deltaG of the reactions of oxidation with oxygen and reduction with hydrogen are included:

$$4Mn_3O_4 + O_2 \rightarrow 6Mn_2O_3$$

$$2Mn_2O_3 + O_2 \rightarrow 4MnO_2$$

$$6MnO + O_2 \rightarrow 2Mn_3O_4 \quad \Delta G = -15.7 \text{ kcal/mole}$$

$$Mn_3O_4 + H_2 = 3MnO + H_2O \quad \Delta G = -2.5 \text{ kcal/mole}$$

Difference would be −13.2 kcal/mole

The larger the difference in the ΔG there is less probability of reduction back to the lower oxidation state and therefore there is less possibility of water generation. The details of different manganese oxide and their ΔG/metal atom of oxidation w/$O_2$ and reduction w/$H_2$ at different temperatures are illustrated in Table 2 below.

TABLE 2

| | Difference between ΔG/Metal Atom of Oxidation w/$O_2$ and Reduction w/$H_2$ | | |
|---|---|---|---|
| Temperature | MnO/$Mn_3O_4$ | $Mn_3O_4$/$Mn_2O_3$ | $Mn_2O_3$/$MnO_2$ |
| 0 | −13.2 | 3.4 | 14.6 |
| 100 | −11.5 | 3.8 | 16.6 |
| 200 | −9.9 | 4.3 | 18.6 |
| 300 | −8.3 | 4.8 | 20.5 |
| 400 | −6.7 | 5.2 | 22.4 |

A relationship exists between the contact time and resulting oxygen concentration in the product stream. For a relatively short contact time, the absorbent may not have sufficient time to react chemically and thus remove all the oxygen present, but with longer time the oxygen may be removed to very low concentration such as 0.1 ppm or less. Also for low oxygen concentrations in the feed gas stream, very low oxygen concentrations in the product gas can be achieved even with short contact times. Thus, in general, for a particular desired concentration in the effluent product stream, the contact time required is roughly inversely proportional to the oxygen concentration in the feed stream.

While the subject matter has been described with what are presently considered the preferred embodiments, it is to be understood that the subject matter is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for removing oxygen from an oxygen containing gas mixture comprising the steps of providing a partially oxidized form of manganese carbonate, iron carbonate, nickel carbonate and/or cobalt carbonate contacting said partially oxidized form of manganese carbonate with said gas mixture; and adsorbing said oxygen from the gas mixture without generating water to produce a purified gas. An embodiment of the invention is one, any or all of prior embodiments in this paragraph up through the first embodiment in this paragraph wherein said adsorption is carried out at a temperature from about 20° C. to about 200° C. An embodiment of the invention is one, any or all of prior embodiments in this paragraph up through the first embodiment in this paragraph wherein said partially oxidized form of manganese carbonate has a crystallite size of less than about 0.08 microns. An embodiment of the invention is one, any or all of prior embodiments in this paragraph up through the first embodiment in this paragraph wherein said gas mixture comprises from about 1 to about 100 ppm oxygen. An embodiment of the invention is one, any or all of prior embodiments in this paragraph up through the first embodiment in this paragraph wherein said gas mixture further comprises hydrocarbons. An embodiment of the invention is one, any or all of prior embodiments in this paragraph up through the first embodiment in this paragraph wherein said hydrocarbons comprise methane. An embodiment of the invention is one, any or all of prior embodiments in this paragraph up through the first embodiment in this paragraph wherein said gas mixture further comprises hydrogen and carbon monoxide. An embodiment of the invention is one, any or all of prior embodiments in this paragraph up through the first embodiment in this paragraph wherein said purified gas contains no more than 0.1 ppm oxygen.

A second embodiment of the invention is a process for preparing an improved adsorbent for removing oxygen comprising providing a precursor selected from the group consisting of manganese carbonate, iron carbonate, nickel carbonate, and cobalt carbonate; adding and mixing 15-20% water to the precursor to generate a LOI of 45-55% to prepare a mixture; mixing and forming; drying the mixture to about 0.5-3% water; and partially decomposing to suboxide the said precursor. An embodiment of the invention is one, any or all of prior embodiments in this paragraph up through the second embodiment in this paragraph wherein an improved adsorbent is prepared by the method of second embodiment.

Without further elaboration, it is believed that using the preceding description that one skilled in the art can utilize the present invention to its fullest extent and easily ascertain the essential characteristics of this invention, without departing from the spirit and scope thereof to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for removing oxygen from an oxygen containing gas mixture comprising the steps of:
   providing a partially oxidized form of a metal carbonate selected from the group consisting of manganese carbonate, iron carbonate, nickel carbonate and cobalt carbonate, wherein said partially oxidized form of metal carbonate has a crystallite particle size of less than about 0.08 microns;
   contacting said partially oxidized form of metal carbonate with said gas mixture; and
   adsorbing said oxygen from the gas mixture without generating water to produce a purified gas.

2. The process of claim 1 wherein said adsorption is carried out at a temperature from about 20° C. to about 200° C.

3. The process of claim 1 wherein said gas mixture comprises from about 1 to about 100 ppm oxygen.

4. The process of claim 1 wherein said gas mixture further comprises hydrocarbons.

5. The process of claim 4 wherein said hydrocarbons comprise methane.

6. The process of claim 1 wherein said gas mixture further comprises hydrogen and carbon monoxide.

7. The process of claim 1 wherein said purified gas contains no more than about 0.1 ppm oxygen.

* * * * *